(12) United States Patent
Tzeng et al.

(10) Patent No.: US 7,618,998 B2
(45) Date of Patent: Nov. 17, 2009

(54) ISOFLAVONE DERIVATIVES AND PHARMACEUTICAL COMPOSITIONS COMPRISING THE SAME

(75) Inventors: Cherng-Chyi Tzeng, Kaohsiung (TW); Yeh-Long Chen, Kaohsiung (TW); Gwo-Jaw Wang, Kaohsiung (TW); Mei-Ling Ho, Kaohsiung (TW); Je-Ken Chang, Kaohsiung (TW); Yin-Chih Fu, Kaohsiung (TW)

(73) Assignee: Kaosiung Medical University, Kaohsiung (TW)

( * ) Notice: Subject to any disclaimer, the term of this patent is extended or adjusted under 35 U.S.C. 154(b) by 0 days.

(21) Appl. No.: 12/241,671

(22) Filed: Sep. 30, 2008

(65) Prior Publication Data

US 2009/0215767 A1  Aug. 27, 2009

(30) Foreign Application Priority Data

Feb. 26, 2008  (TW) .............................. 97106589 A

(51) Int. Cl.
*A61K 31/35* (2006.01)
(52) U.S. Cl. ..................................... 514/456
(58) Field of Classification Search .................. 514/456
See application file for complete search history.

(56) References Cited

U.S. PATENT DOCUMENTS

| | | | |
|---|---|---|---|
| 4,501,755 A | 2/1985 | Wu | |
| 4,668,804 A | 5/1987 | Wu | |
| 5,247,102 A | 9/1993 | Kallay et al. | |
| 5,973,169 A | 10/1999 | Ferrari | |
| 2006/0100238 A1 | 5/2006 | Kelly et al. | |

FOREIGN PATENT DOCUMENTS

| | | |
|---|---|---|
| CN | 1475488 A | 2/2004 |
| CN | 1603318 A | 4/2005 |
| EP | 0136569 A2 | 4/1985 |
| EP | 0941992 A1 | 9/1999 |
| EP | 0941992 B1 | 5/2002 |
| JP | 09-268187 | 10/1997 |
| JP | 11-012265 | 1/1999 |
| WO | WO-91/15483 | 10/1991 |
| WO | WO-91-15483 | 10/1991 |
| WO | WO-95/03293 | 2/1995 |
| WO | WO-98/29403 | 7/1998 |

OTHER PUBLICATIONS

Xiao et al., "Polyphenols based on isoflavones as inhibitors of *Helicobacter pylori* urease," Bioorganic & Medicinal Chemistry, 2007, pp. 3703-3710, 15.
Stachulski et al., "Identification of Isoflavone Derivatives as Effective Anticryptosporidal Agents in Vitro and in Vivo," J. Med. Chem., 2006, pp. 1450-1454, 49.
Vasselin et al., "Structural Studies on Bioactive Compounds. 40. Synthesis and Biological Properties of Fluoro-. Methoxyl-, and Amino-Substituted 3-Phenyl-4H-1-benzopyran-4-ones and a Comparison of Their Antitumor Activities with the Acitivies of Related 2-Phenylbenzothiazoles," J. Med. Chem., 2006, pp. 3973-3981, 49.
Aggarwal et al., "Molecular targets of dietary agents for prevention and therapy of cancer," Biochemical Pharmacology, 2006, pp. 1397-1421, 71.
Ren et al.,"Flavonoids: Promising Anticancer Agents," Medical Research Reviews, 2003, pp. 519-534, vol. 23, No. 4.
Wang et al., "Genistein derivatives as selective estrogen receptor modulators: Sonochemical synthesis and in vivo anti-osteoporotic action," Biochemical & Medicinal Chemistry, 2005, pp. 4880-4890, 13.
Ishimi et al., "Genistein, a Soybean Isoflavone, Affects Bone Marrow Lymphopoeisis and Prevents Bone Loss in Castrated Male Mice," Bone, 2002, pp. 180-185, vol. 31, No. 1.
Morabito et al., "Effects of Genistein and Hormone-Replacement Therapy on Bone Loss in Early Postmenopausal Women: A Radomized Double-Blind Placebo-Controlled Study," Journal of Bone and Mineral Research, 2002, pp. 1904-1912, vol. 17, No. 10.
Delcanale et al., "Novel Basic Isoflavones as Inhibitors of Bone Resorption," Helvetica Chimica Acta, 2001, pp. 2417-2429, 84.
Wang et al., "Synthesis, antiproliferative, and antiplatelet activities of oxime- and methyloxime-containing flavone and isoflavone derivtives," Bioorganic & Medicinal Chemistry, 2005, pp. 6045-6053, 13.

(Continued)

*Primary Examiner*—Raymond J Henley, III
(74) *Attorney, Agent, or Firm*—Muncy, Geissler, Olds & Lowe, PLLC

(57) ABSTRACT

An isoflavone derivative is provided. The isoxazole derivative has following formula:

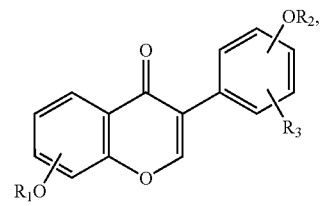

wherein $R_1$ and $R_2$, independently, include $C_1$-$C_{12}$ alkyl optionally substituted with oxirane, thiirane, aziridine, amino, cycloamino, aminohydroxy or cycloaminohydroxy, and $R_3$ includes hydrogen, hydroxy or $C_1$-$C_{12}$ alkoxy optionally substituted with oxirane, thiirane, aziridine, amino, cycloamino, aminohydroxy or cycloaminohydroxy. The invention also provides a pharmaceutical composition for treatment of osteoporosis including an isoflavone derivative or a pharmaceutically acceptable salt thereof and a pharmaceutically acceptable carrier.

3 Claims, No Drawings

OTHER PUBLICATIONS

Gao et al., "Synthesis of Daidzin Analogues as Potential Agents for Alcohol Abuse," Bioorganic & Medicinal Chemistry, 2003, pp. 4069-4081, 11.

Carmichael et al., "Evaluation of a Tetrazolium-based Semiautomated Colorimetric Assay: Assessment of Chemosensitivity Testing," Cancer Research, Feb. 15, 1987, pp. 936-942, 47.

Crowston et al., "Antimetabolite-Induced Apoptosis in Tenon's Capsule Fibroblasts," IOVS, Feb. 1998, pp. 449-454, vol. 39, No. 2.

Gregory et al., "An Alizarin red-based assay of mineralization by adherent cells in culture:comparison with cetylpyridinum chloride extraction," Analytical Biochemistry, 2004, pp. 77-84, 329.

Wu et al., "Flavones. 3. Synthesis, Biological Activities, and Conformational Analysis of Isoflavone Derivatives and Related Compounds," J. Med. Chem., 1992, pp. 3519-3525, 35.

Kikuchi et al., "Brandisianins A-F, Isoflavonoids Isolated from *Millettia brandisiana* in a Screening Program for Death-Receptor Expression Enhancement Activity," J. Nat. Prod., 2007, pp. 1910-1914, 70.

Alexandersen el al., "Ipriflavone in Treatment of Postmenopausal Osteoporosis," JAMA, Mar. 21, 2001, pp. 1482-1488, vol. 285, No. 11.

Amari et al., "Synthesis, pharmacological evaluation, and structure-activity relationships of benzopyran derivatives with potent SERM activity," Bioorganic & Medicinal Chemistry, 2004, pp. 3763-3782, 12.

ISOFLAVONE DERIVATIVES AND PHARMACEUTICAL COMPOSITIONS COMPRISING THE SAME

This Application claims priority of Taiwan Patent Application No. 97106589, filed on Feb. 26, 2008, the entirety of which is incorporated by reference herein.

BACKGROUND OF THE INVENTION

1. Field of the Invention

The invention relates to a compound, and in particular, to an isoflavone derivative for treatment of osteoporosis.

2. Description of the Related Art

Isoflavonoids are presented in large quantities in soybeans and soy products. These natural products along with their synthetic analogues possess a wide variety of biological effects including antiparasitic, antiproliferative, antifungal, antiviral, anti-inflammatory, antioxidant, and cardiovascular effects (Xiao, Z. P. et al., *Bioorg. Med. Chem.*, 2007, 15, 3703; Stachulski, A. V. et. al. *J. Med. Chem.* 2006, 49, 1450; Vasselin, D. A. et. al. *J. Med. Chem.* 2006, 49, 3973; Aggarwal, B. B. et. al. *Biochem. Pharmacol.* 2006, 71, 1397; Qing, F. et. al. Patent No. CN 2003/1475488 A; Wu, E. S. Patent No. US 1986/4668804 A; Chapman and Hall; London, 1999; Ren, W. et. al., *Med. Res. Rev.* 2003, 23, 519).

Genistein, a major isoflavone phytochemical in some plants, is known as a phytoestrogen that is capable of binding to the estrogen receptor. Much attention has been focused on the role of genistein in preventing bone loss resulting at least, in part from estrogen deficiency (Tan, R. et. al., Patent No. CN 2004/1603318 A; Wang, S. F. et al., *Bioorg. Med. Chem.*, 2005, 13, 4880; Ishimi, Y., et. al., Bone, 2002, 31, 180; Morabito, N. et. al., *J. Bone Miner Res.*, 2002, 17, 1904).

Ipriflavone (Kunikata, K. et. al. Patent No. JP 1996/09268187 A; Imamiya, K. et. al. Patent No. JP 1997/11012265 A; Yamazaki, I. et. al. Patent No. EP 1984/136569 A2; Ferrari, M. Patent No. EP 1999/941992 A1; Ferrari, M. Patent No. EP 2002/941992 B1), one of the synthetic isoflavone derivatives, has been approved for the treatment of involutional osteoporosis in some European countries and in Japan. However, only few reports have been dedicated to the improvement of the selective estrogen receptor modulator (SERM) activity and the anti-osteoporotic activity of isoflavone derivatives (Chiest, P. et. al. Patent No. WO 98/29403; Delcanale, M. et. al., *Helv. Chim. Acta* 2001, 84, 2417; Kelly, G. E. et. al., Patent No. US 2006/0100238 A1).

BRIEF SUMMARY OF THE INVENTION

One embodiment of the invention provides an isoflavone derivative having the following formula:

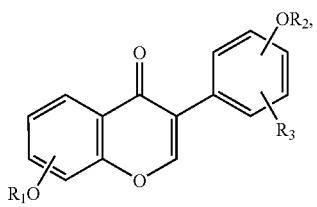

wherein $R_1$ and $R_2$, independently, comprise $C_1$-$C_{12}$ alkyl optionally substituted with oxirane, thiirane, aziridine, amino, cycloamino, aminohydroxy or cycloaminohydroxy, and $R_3$ comprises hydrogen, hydroxy or $C_1$-$C_{12}$ alkoxy optionally substituted with oxirane, thiirane, aziridine, amino, cycloamino, aminohydroxy or cycloaminohydroxy.

One embodiment of the invention provides a pharmaceutical composition comprising a disclosed isoflavone derivative or a pharmaceutically acceptable salt thereof and a pharmaceutically acceptable carrier.

One embodiment of the invention provides a pharmaceutical composition for treatment of osteoporosis comprising a disclosed isoflavone derivative or a pharmaceutically acceptable salt thereof and a pharmaceutically acceptable carrier.

A detailed description of the invention is provided in the following.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides an isoflavone derivative having the following formula:

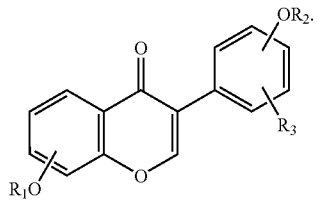

In the formula, $R_1$ and $R_2$ may, independently, comprise $C_1$-$C_{12}$ alkyl optionally substituted with oxirane, thiirane, aziridine, amino, cycloamino, aminohydroxy or cycloaminohydroxy. $R_3$ may comprise hydrogen, hydroxy or $C_1$-$C_{12}$ alkoxy optionally substituted with oxirane, thiirane, aziridine, amino, cycloamino, aminohydroxy or cycloaminohydroxy.

The isoflavone derivative may be present as a hydrate or as a stereoisomer.

One embodiment of the invention provides a pharmaceutical composition comprising a disclosed isoflavone derivative or a pharmaceutically acceptable salt thereof and a pharmaceutically acceptable carrier.

One embodiment of the invention provides a pharmaceutical composition for treatment of osteoporosis comprising a disclosed isoflavone derivative or a pharmaceutically acceptable salt thereof and a pharmaceutically acceptable carrier.

The pharmaceutically acceptable salts may comprise salts with inorganic acids such as hydrochloride, hydrobromide, sulfate and phosphate, with organic acids such as acetate, maleate, tartrate and methanesulfonate, and with amino acids such as arginine, aspartic acid and glutamic acid.

The pharmaceutically acceptable carrier may comprise any and all solvents, disintegrating agents, binders, excipients, lubricants, absorption delaying agents and the like.

The isoflavone derivative and its pharmaceutical composition effectively treat osteoporosis. They may be administered parenterally or orally in a suitable pharmaceutical form, for example, sterile aqueous solutions or dispersions, sterile powders, tablets, troches, pills, capsules or the like. They may also be administered along or in conjugation with other anti-osteoporotic and/or anticancer agents, or in combination with any pharmaceutically acceptable carrier. In addition, the pharmaceutical composition may be incorporated into sustained-release preparations and formulations.

The isoflavone derivative is prepared according to the following reaction scheme 1.

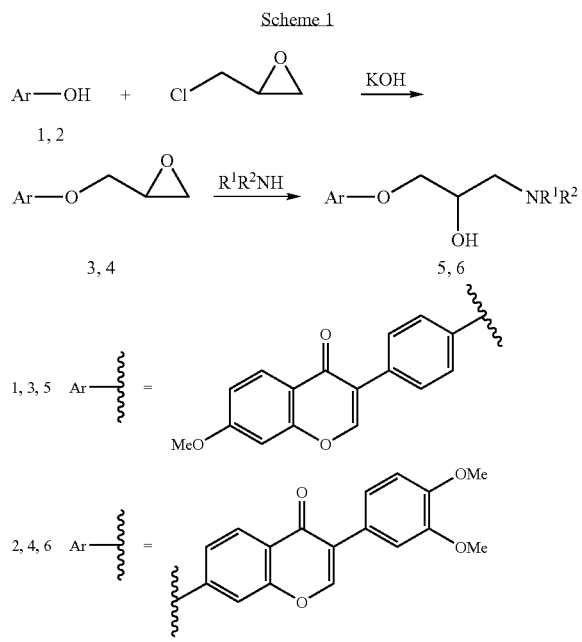

As described in Scheme 1, reaction of 3-(4-hydroxyphenyl)-7-methoxy-4H-chromen-4-one (1) and 7-hydroxy-3-(3,4-dimethoxyphenyl)-4H-chromen-4-one (2), respectively, with epichlorohydrin gives the respective 2,3-epoxypropoxyisoflavones 3,4 which are respectively treated with substituted amines to afford the respective 3-amino-2-hydroxypropoxyisoflavones 5,6.

EXAMPLE 1

Preparation of 7-Methoxy-3-[4-(oxiran-2-ylmethoxy)phenyl]-4H-chromen-4-one (3)

A mixture of 7-methoxy-4'-hydroxyisoflavone (1, 0.27 g, 1 mmol), $K_2CO_3$ (0.41 g, 3 mmol), epichlorohydrin (0.3 g, 3 mmol) and acetonitrile (30 mL) was refluxed with stirring for 4 hrs (TLC monitoring). The mixture was evaporated in vacuo to give a residue which was treated with $H_2O$ (50 mL). The precipitate thus formed was collected, purified by column chromatography (MeOH/$CH_2Cl_2$=1:50), and crystallized from EtOH to give the title compound 3 (0.14 g, 43% yield). M.p.: 153-154° C.

$^1$H-NMR (400 MHz, DMSO-$d_6$): 2.72 (dd, 1H, J=2.8, 5.2 Hz), 2.85 (dd, 1H, J=4.4, 4.8 Hz), 3.33-3.34 (m, 1H), 3.86 (dd, 1H, J=6.4, 11.2 Hz), 3.90 (s, 3H, OMe), 4.37 (dd, 1H, J=2.4, 11.2 Hz), 7.02 (d, 2H, J=8.8 Hz), 7.08 (dd, 1H, J=2.8, 9.2 Hz), 7.15 (d, 1H, J=2.0 Hz), 7.2 (d, 2H, J=8.8 Hz), 8.02 (d, 1H, J=8.8 Hz), 8.42 (s, 1H). $^{13}$C-NMR (100 MHz, DMSO-$d_6$): 43.78, 49.74, 56.12, 68.99, 100.56, 114.22 (2C), 114.81, 117.58, 123.29, 124.45, 126.95, 130.11 (2C), 153.56, 157.46, 157.99, 163.73, 174.63. Anal. calcd for $C_{19}H_{16}O_5$: C, 70.36; H, 4.97. Found: C, 70.46; H, 4.95.

EXAMPLE 2

Preparation of 3-(3,4-Dimethoxyphenyl)-7-(oxiran-2-ylmethoxy)-4H-chromen-4-one (4)

A mixture of 7-hydroxy-3',4'-dimethoxyisoflavone (2, 0.30 g, 1 mmol), $K_2CO_3$ (0.41 g, 3 mmol), epichlorohydrin (0.3 g, 3 mmol) and acetonitrile (30 mL) was refluxed with stirring for 4 hrs (TLC monitoring). The mixture was evaporated in vacuo to give a residue which was treated with $H_2O$ (50 mL). The precipitate thus formed was collected, purified by column chromatography (MeOH/$CH_2Cl_2$=1:100), and crystallized from EtOH to give the title compound 4 (0.25 g, 70% yield). M.p.: 161-162° C.

$^1$H-NMR (400 MHz, CDCl$_3$): 2.81 (dd, 1H, J=2.8, 5.2 Hz), 2.96 (dd, 1H, J=4.4, 4.8 Hz), 3.40-3.44 (m, 1H), 3.92 (s, 3H, OMe), 3.93 (s, 3H, OMe), 4.03 (dd, 1H, J=6.0, 11.2 Hz), 4.38 (dd, 1H, J=2.8, 11.2 Hz), 6.90 (d, 1H, J=2.4 Hz), 6.92 (d, 1H, J=8.0 Hz), 7.02-7.06 (m, 2H), 7.20 (d, 1H, J=1.6 Hz), 7.95 (s, 1H), 8.21 (d, 1H, J=8.8 Hz). $^{13}$C-NMR (100 MHz, CDCl$_3$): 44.53, 49.76, 55.92, 55.94, 69.28, 101.04, 111.12, 112.45, 114.73, 118.75, 121.00, 124.53, 124.96, 127.90, 148.74, 149.08, 152.29, 157.73, 162.69, 175.83. Anal. calcd for $C_{20}H_8O_6$·1.0$H_2O$·0.8HCl: C, 59.81; H, 5.23. Found: C, 59.90; H, 5.46.

EXAMPLE 3

Preparation of 3-[4-(2-Hydroxy-3-morpholinopropoxy)phenyl]-7-methoxy-4H-chromen-4-one (5a)

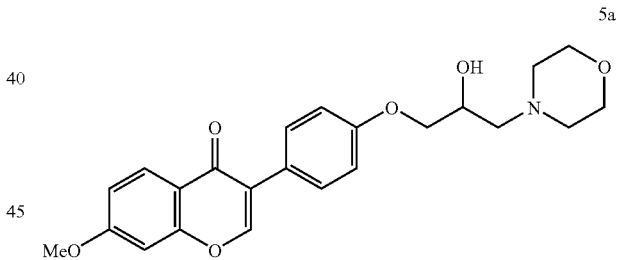

A mixture of compound 3 (obtained from example 1) (0.32 g, 1 mmol), morpholine (0.43 g, 5 mmol), and ethanol (30 mL) was refluxed for 4 hrs (TLC monitoring). After removal of solvent in vacuo, the residue was treated with $H_2O$ (50 mL). The resulting precipitate was collected and purified by column chromatography (MeOH/$CH_2Cl_2$=1:20) to give the title compound 5a (0.28 g, 68% yield). M.p.: 117-118° C.

$^1$H-NMR (400 MHz, CDCl$_3$): 2.48-2.52 (m, 2H), 2.57-2.61 (m, 2H), 2.66-2.72 (m, 2H), 3.73-3.76 (m, 4H), 3.92 (s, 3H, OMe), 4.03 (d, 2H, J=4.8 Hz), 4.11-4.17 (m, 1H), 6.85 (d, 1H, J=2.4 Hz), 6.97-7.01 (m, 3H), 7.48-7.51 (d, 2H, J=8.4 Hz), 7.92 (s, 1H), 8.20 (d, 1H, J=8.8 Hz). $^{13}$C-NMR (100 MHz, CDCl$_3$): δ3.75, 55.81, 61.02, 65.37, 66.97 (3C), 70.22, 94.38, 100.07, 114.55, 114.58, 118.38, 124.62, 124.78, 127.77, 130.15 (2C), 152.10, 157.94, 158.65, 163.97, 175.85. Anal. calcd for $C_{23}H_{25}NO_6$: C, 66.40; H, 6.19; N, 3.37. Found: C, 66.09; H, 6.17; N, 3.34.

EXAMPLE 4

Preparation of 3-{4-[3-(Cyclopropylamino)-2-hydroxypropoxy]phenyl-7-methoxy-4H-chromen-4-one (5b)

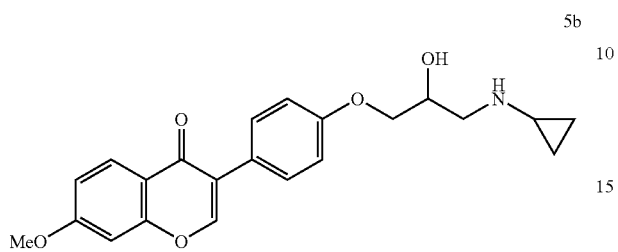

A mixture of compound 3 (obtained from example 1) (0.32 g, 1 mmol), cyclopropylamine (0.29 g, 5 mmol), and ethanol (30 mL) was refluxed for 4 hrs (TLC monitoring). After removal of solvent in vacuo, the residue was treated with $H_2O$ (50 mL). The resulting precipitate was collected and purified by column chromatography (MeOH/$CH_2Cl_2$=1:20) to give the title compound 5b (0.30 g, 78% yield). M.p.: 105-106° C.

$^1$H-NMR (400 MHz, DMSO-$d_6$): 0.22 (m, 2H), 0.36 (m, 2H), 2.11 (m, 1H), 2.66 (dd, 1H, J=6.4, 12.0 Hz), 2.74 (dd, 1H, J=4.0, 12.0 Hz), 3.88-4.05 (m, 6H), 4.97 (br s, 1H, NH), 6.99 (d, 2H, J=8.4 Hz), 7.09 (dd, 1H, J=2.4, 9.2 Hz), 7.17 (d, 1H, J=2.0 Hz), 7.51 (d, 2H, J=8.4 Hz), 8.03 (d, 1H, J=8.4 Hz), 8.43 (s, 1H). $^{13}$C-NMR (100 MHz, DMSO-$d_6$): 6.17 (2C), 30.29, 52.21, 56.13, 67.95, 70.83, 100.07, 114.20 (2C), 114.80, 117.59, 123.38, 124.00, 126.95, 130.05 (2C), 153.48, 157.46, 158.52, 163.71, 174.65. Anal. calcd for $C_{22}H_{23}NO_5.0.1H_2O$: C, 68.94; H, 6.11; N, 3.66. Found: C, 68.69; H, 6.06; N, 3.46.

EXAMPLE 5

Preparation of 3-{4-[3-(Cyclohexylamino)-2-hydroxypropoxy]phenyl}-7-methoxy-4H-chromen-4-one (5c)

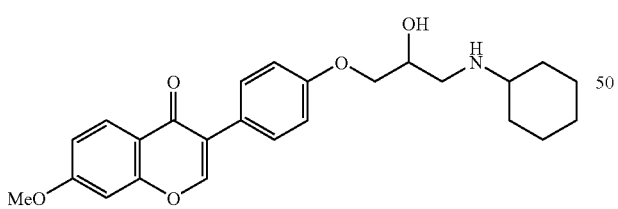

A mixture of compound 3 (obtained from example 1) (0.32 g, 1 mmol), cyclohexylamine (0.50 g, 5 mmol), and ethanol (30 mL) was refluxed for 4 hrs (TLC monitoring). After removal of solvent in vacuo, the residue was treated with $H_2O$ (50 mL). The resulting precipitate was collected and purified by column chromatography (MeOH/$CH_2Cl_2$=1:20) to give the title compound 5c (0.28 g, 67% yield). M.p.: 125-126° C.

$^1$H-NMR (400 MHz, CDCl$_3$): 1.05-1.32 (m, 5H), 1.60-1.64 (m, 1H), 1.73-1.77 (m, 2H), 1.92-1.95 (m, 2H), 2.43-2.51 (m, 1H), 2.74 (dd, 1H, J=8.0, 12.4 Hz), 2.95 (dd, 1H, J=3.6, 12.4 Hz), 3.92 (s, 3H, OMe), 3.97-4.08 (m, 3H), 6.85 (d, 1H, J=2.4 Hz), 6.96-7.01 (m, 3H), 7.48 (d, 2H, J=8.8 Hz), 7.92 (s, 1H), 8.19 (d, 1H, J=8.8 Hz). $^{13}$C-NMR (100 MHz, CDCl$_3$): 24.97 (2C), 25.99, 33.44, 33.67, 48.74, 55.81, 56.82, 68.26, 70.52, 100.05, 114.54 (2C), 114.57, 118.37, 124.54, 124.78, 127.76, 130.13 (2C), 152.09, 157.93, 158.67, 163.95, 175.84. Anal. calcd for $C_{25}H_{29}NO_5.0.1H_2O$: C, 70.59; H, 6.93; N, 3.29. Found: C, 70.38; H, 6.87; N, 3.29.

EXAMPLE 6

Preparation of 3-(3,4-Dimethoxyphenyl)-7-(2-hydroxy-3-morpholinopropoxy)-4H-chromen-4-one (6a)

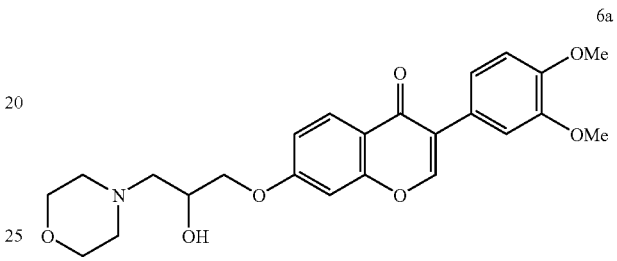

A mixture of compound 4 (obtained from example 2) (0.35 g, 1 mmol), morpholine (0.43 g, 5 mmol), and ethanol (30 mL) was refluxed for 6 hrs (TLC monitoring). After removal of solvent in vacuo, the residue was treated with $H_2O$ (50 mL). The resulting precipitate was collected and purified by column chromatography (MeOH/$CH_2Cl_2$=1:25) to give the title compound 6a (0.23 g, 51% yield). M.p.: 135-136° C.

$^1$H-NMR (400 MHz, CDCl$_3$): 2.47-2.73 (m, 6H), 3.54 (br s, 1H, OH), 3.71-3.80 (m, 4H), 3.92 (s, 3H, OMe), 3.93 (s, 3H, OMe), 4.07-4.11 (m, 2H), 4.13-4.20 (m, 1H), 6.90 (d, 1H, J=2.4 Hz), 6.92 (d, 1H, J=8.4 Hz), 7.02-7.06 (m, 2H), 7.20 (d, 1H, J=2.0 Hz), 7.95 (s, 1H), 8.20 (d, 1H, J=8.8 Hz). $^{13}$C-NMR (100 MHz, CDCl$_3$): 30.85, 53.69, 55.91, 55.93, 60.78, 65.08, 66.92 (2C), 70.67, 100.89, 111.12, 112.45, 114.77, 118.61, 121.00, 124.54, 124.93, 127.80, 148.73, 149.07, 152.26, 157.75, 162.99, 175.83. Anal. calcd for $C_{24}H_{27}NO_7$: C, 65.29; H, 6.16; N, 3.17. Found: C, 65.20; H, 6.19; N, 3.14.

EXAMPLE 7

Preparation of 3-(3,4-Dimethoxyphenyl)-7-[2-hydroxy-3-(piperazin-1-yl)propoxy]-4H-chromen-4-one (6b)

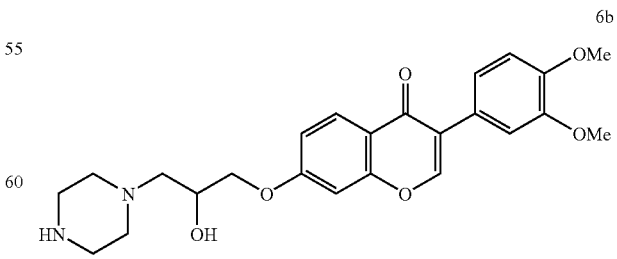

A mixture of compound 4 (obtained from example 2) (0.35 g, 1 mmol), piperazine (0.43 g, 5 mmol), and ethanol (30 mL) was refluxed for 6 hrs (TLC monitoring). After removal of solvent in vaccuo, the residue was treated with $H_2O$ (50 mL). The resulting precipitate was collected and purified by column chromatography ($MeOH/CH_2Cl_2$=1:25) to give the title compound 6b (0.25 g, 56% yield). M.p.: 84-85° C.

$^1$H-NMR (400 MHz, $CDCl_3$): 2.45-2.68 (m, 7H), 2.88-2.96 (m, 3H), 3.92 (s, 3H, OMe), 3.93 (s, 3H, OMe), 4.05-4.17 (m, 3H), 6.89 (d, 1H, J=2.4 Hz), 6.92 (d, 1H, J=8.0 Hz), 7.01-7.06 (m, 2H), 7.21 (d, 1H, J=2.0 Hz), 7.95 (s, 1H), 8.19 (d, 1H, J=8.8 Hz). $^{13}$C-NMR (100 MHz, $CDCl_3$): 30.84, 46.05, 54.50, 55.84, 55.86, 60.80, 64.99, 65.13, 70.81, 100.80, 111.04, 112.38, 114.77, 118.46, 120.94, 124.51, 124.82, 127.67, 148.65, 148.98, 152.21, 157.69, 163.03, 175.77. Anal. calcd for $C_{24}H_{28}N_2O_6 \cdot 0.5H_2 \cdot 0.5HCl$: C, 61.62; H, 6.37; N, 5.99. Found: C, 61.92; H, 6.75; N, 5.62.

EXAMPLE 8

Preparation of 7-[3-(Cyclohexylamino)-2-hydroxypropoxy]-3-(3,4-dimethoxyphenyl)-4H-chromen-4-one (6c)

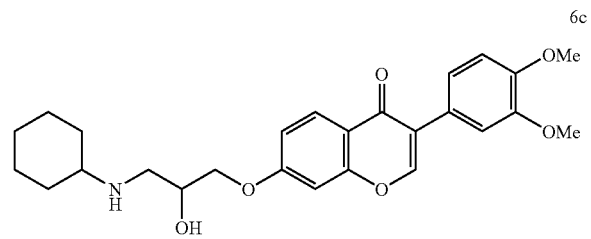

A mixture of compound 4 (obtained from example 2) (0.35 g, 1 mmol), cyclohexylamine (0.50 g, 5 mmol), and ethanol (30 mL) was refluxed for 6 hrs (TLC monitoring). After removal of solvent in vacuo, the residue was treated with $H_2O$ (50 mL). The resulting precipitate was collected and purified by column chromatography ($MeOH/CH_2Cl_2$=1:25) to give the title compound 6c (0.24 g, 54% yield). M.p.: 70-71° C.

$^1$H-NMR (400 MHz, $CDCl_3$): 1.06-1.32 (m, 5H), 1.61-1.65 (m, 1H), 1.72-1.77 (m, 2H), 1.92-1.95 (m, 2H), 2.42-2.48 (m, 1H), 2.76 (dd, 1H, J=8.0, 12.4 Hz), 2.96 (dd, 1H, J=3.6, 12.4 Hz), 3.92 (s, 3H, OMe), 3.93 (s, 3H, OMe), 4.03-4.08 (m, 3H), 6.89 (d, 1H, J=2.4 Hz), 6.92 (d, 1H, J=8.4 Hz), 7.02 (dd, 1H, J=2.4, 8.8 Hz), 7.04 (dd, 1H, J=2.4, 8.4 Hz), 7.20 (d, 11H, J=2.4 Hz), 7.95 (s, 1H), 8.20 (d, 1H, J=8.8 Hz). $^{13}$C-NMR (100 MHz, $CDCl_3$): 24.96 (2C), 25.98, 33.61, 33.91, 48.52, 55.90, 55.92, 56.75, 68.04, 71.04, 100.82, 111.09, 112.42, 114.82, 118.53, 120.99, 124.55, 124.90, 127.75, 148.70, 149.04, 152.26, 157.77, 163.05, 175.86. Anal. calcd for $C_{26}H_{31}NO_6 \cdot 0.2H_2O$: C, 68.32; H, 6.92; N, 3.06. Found: C, 68.51; H, 6.99; N, 3.01.

EXAMPLE 9

Tartrate Resistant Acid Phosphatase (TRAP) Solution Assay $10^3$ Raw 264.7 cells were cultured in 96-well plates with 100 ng/mL RANKL (R&D Systems, Minneapolis, Minn.). Cultures were incubated at 37° C. in 5% $CO_2$ for 5 days with the addition of media containing fresh RANKL on day 3. In the TRAP solution assay, enzyme activity was examined by the conversion of α-naphthyl phosphate (4 mmol/liter; Sigma Chemical Co.) to α-naphthol in the presence of a 2 mol/liter L-tartrate solution (Sigma Chemical Co.) in each well. Absorbance was measured at 405 nm using a microplate reader (model 550; Bio-Rad Labs.) (Bandyopadhyay, S. et. el. *Biochem. Pharmacol.* 2006, 72, 184.).

EXAMPLE 10

Cell Culture and Drug Treatment

D1-cell, which is a mesenchymal stem cell line cloned from bone marrow cells of Balb/c mice, were purchased from American Type Culture Collection (Rockville, Md.). D1-cells can be induced into osteoblasts, adipocytes and chondrocytes. D1-cells were maintained in DMEM (Gibco BRL, Gaithersburg, Md.) supplemented with 10% FBS, 100 U/ml of penicillin and streptomycin.

MC3T3E1 cell, which is a preosteoblast cell line derived from calvaria of C57BL/6 mice, were obtained from the American Type Culture Collection (Rockville, Md.). MC3T3E1 cells were maintained in αMEM (Gibco BRL, Gaithersburg, Md.) supplemented with 10% FBS, 100 U/mL of penicillin and streptomycin.

Human adipose tissue derived stem cells (hADSCs), which is derived from adipose tissue, were selected an maintained in a keratinocyte SFM medium (Gibco BRL, Gaithersburg, Md.) supplemented with 5% FBS, 100 U/ml of penicillin and streptomycin. They exhibited osteogenic properties in the Dulbecco modified Eagle medium (Gibco BRL, Gaithersburg, Md.) containing 10% fetal bovine serum and 50 μg/mL sodium ascorbate in a humidified atmosphere of 5% $CO_2$ at 37° C., wherein the medium was changed every 2 days.

New synthetic compounds were dissolved in DMSO to a final concentration of 10 mM and stored at −20° C. The concentration used was 10 μM and freshly diluted to the medium with a final concentration of DMSO at 0.1%. Control cultures were treated with the same amount of DMSO as used in the corresponding experiments.

EXAMPLE 11

Cell viability by MTT [3-(4,5-dimethylthiazol-2-yl)-2,5-diphenyltetrazolium bromide] assay The MTT assay is a calorimetric assay based on the ability of the viable cells to reduce a soluble yellow tetrazolium salt to blue formazan crystals (Carmichael, J. et. el. *Cancer Research* 1987, 47, 936). After compound treatments, 350 μL of MTT solution (0.5 μg/mL in PBS) were added to each well and incubated for 4 hrs. DMSO was then added for another 0.5 hrs to thoroughly dissolve the dark blue crystals. The absorbance at 570 nm was measured with an ELISA reader. Inhibition of mitochondrial metabolism was shown as relative activity (% of control).

EXAMPLE 12

Osteogenic Differentiation and Quantification of Mineralization

Osteogenic differentiation was induced by culturing cells in an osteo-induction medium (OIM, 10% FBS, 0.1 μM dexamethasone, 10 mM β-glycerophosphate, and L-Ascorbic 2 phosphate 100 μM in low glucose DMEM) for 7-14 days. The extracellular matrix calcification was estimated by using an Alizarin red S stain (Carl, A. et al *Anal. Biochem.* 2004, 329, 77). The Alizarin red S-stained mineral was quantified by the osteogenesis quantification kit (CHEMICON®). The results were recited as in Table 2.

It was demonstrated that isoflavone derivatives with an 3-amino-2-hydroxypropoxy side chain, for example, 3-{4-[3-(cyclohexylamino)-2-hydroxypropoxy]phenyl}-7-methoxy-4H-chromen-4-one (5c) exhibited being 4-fold more active than ipriflavone in the osteoclast inhibitory activity (inhibition of TRAP activity in RAW 264.7; Table 1). Compound 5c also exhibited being 10-fold more active than ipriflavone in the promotion of osteoblast activity (mineralization in MC3T3E1 cells; Table 2). Compound 5c is a potential anti-osteoporotic drug candidate. In addition to compound 5c, isoflavone derivatives with an oxiran-2-ylmethoxy group, for example, 3-(3,4-dimethoxyphenyl)-7-(oxiran-2-ylmethoxy)-4H-chromen-4-one (4) exhibited comparable anti-osteoporotic activities with that of compound 5c.

TABLE 1

Inhibition of TRAP activity in RAW 264.7 for 5 days by isoflavone derivatives.

| Compd. | NR¹R² | 10 μM (Inhibition %) | $ED_{50}$ (μM) |
|---|---|---|---|
| 3 | — | 107% | 6.39 |
| 4 | — | 119% | <1 |
| 5a | morpholinyl | 0% | ND |
| 5b | cyclopropylamino | 103% | 4.85 |
| 5c | cyclohexylamino | 119% | 2.28 |
| 6a | morpholinyl | 0% | ND |
| 6b | piperazinyl | 0% | ND |
| 6c | cyclohexylamino | 120% | 4.17 |
| Ipriflavone | | 31% | ND |

TABLE 2

Cell viability and mineralization of isoflavone derivatives in D1 cells, MC3T3E1 cells, and hADSCs.

| | Cell viability | | Mineralization | | |
|---|---|---|---|---|---|
| Compd. number | D1 cells (3 days, MTT) | hADSCs (3 days, MTT) | D1 cells (7 days) | MC3T3E1 cells (12 days) | hADSCs (10 days) |
| 4 | 76% | 84% | 112% | 977% | 429% |
| 5c | 82% | 97% | 78% | 976% | ND |
| Ipriflavone | 81% | 99% | 100% | 100% | 100% |

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An isoflavone derivative having following formula:

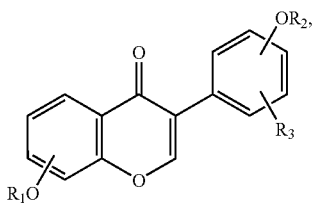

wherein $R_1$ and $R_2$, independently, comprise $C_1$-$C_{12}$ alkyl optionally substituted with oxirane, thiirane, aziridine, amino, cycloamino, aminohydroxy or cycloaminohydroxy; and $R_3$ comprises hydrogen, hydroxy or $C_1$-$C_{12}$ alkoxy optionally substituted with oxirane, thiirane, aziridine, amino, cycloamino, aminohydroxy or cycloaminohydroxy.

2. A pharmaceutical composition, comprising:
an isoflavone derivative as claimed in claim 1 or a pharmaceutically acceptable salt thereof; and
a pharmaceutically acceptable carrier.

3. A pharmaceutical composition for treatment of osteoporosis, comprising:
an isoflavone derivative as claimed in claim 1 or a pharmaceutically acceptable salt thereof; and
a pharmaceutically acceptable carrier.

* * * * *

UNITED STATES PATENT AND TRADEMARK OFFICE
CERTIFICATE OF CORRECTION

PATENT NO. : 7,618,998 B2  Page 1 of 1
APPLICATION NO. : 12/241671
DATED : November 17, 2009
INVENTOR(S) : Cherng-Chyi Tzeng et al.

It is certified that error appears in the above-identified patent and that said Letters Patent is hereby corrected as shown below:

Title page Assignee (73) "KAOSIUNG MEDICAL UNIVERSITY", should be listed as --KAOHSIUNG MEDICAL UNIVERSITY--.

Signed and Sealed this

Twenty-third Day of March, 2010

David J. Kappos
*Director of the United States Patent and Trademark Office*